(12) United States Patent
Thong et al.

(10) Patent No.: US 6,341,234 B1
(45) Date of Patent: Jan. 22, 2002

(54) TRIPOLAR STIMULATION OF HEART CHAMBERS

(75) Inventors: Tran Thong, Portland, OR (US); Max Schaldach, Erlangen (DE)

(73) Assignee: Biotronik Mess-und Therapiegeracte GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 09/335,037

(22) Filed: Jun. 16, 1999

(51) Int. Cl.$^7$ ................................................ A61N 1/362
(52) U.S. Cl. ........................................... 607/9; 607/122
(58) Field of Search ............................ 607/4, 5, 9, 119, 607/122

(56) References Cited

U.S. PATENT DOCUMENTS

| | | |
|---|---|---|
| 4,289,134 A | 9/1981 | Bernstein |
| 5,304,219 A | 4/1994 | Chernoff et al. |
| 5,800,465 A | 9/1998 | Thompson et al. |
| 5,948,014 A | 9/1999 | Valikai |

FOREIGN PATENT DOCUMENTS

| | | |
|---|---|---|
| DE | 32 03 300 C2 | 8/1985 |
| WO | WO 99/13941 | 3/1999 |

OTHER PUBLICATIONS

C.W. Israel et al., "VDD–Schrittmacher in der Terapie des AV–Blocks," DMW 122 (1997), pp. 1189–1194.

A. Prakash et al., *Prediction of outcome of chronic single and dual site right atrial pacing for atrial fibrillation prevention by acute electrophysiologic testing*, PACE, vol. 20, Part II, Apr. 1997, Abstract No. 97.

M. Belham et al., *Bi–atrial pacing for atrial fibrillation: where is the optimal site for left atrial pacing*, PACE, vol. 20, Part II, Apr. 1997, Abstract No. 98.

P. Delfaut et al., *Continuous overdrive pacing prevents recurrent atrial fibrillation during single and dual site right atrial pacing*, PACE, vol. 20, Part II, Apr. 1997, Abstract No. 99.

A. Prakash et al., *Multicenter experience with single and dual site right atrial pacing in refractory atrial fibrillation*, PACE, vol. 20, Part II, Apr. 1997, Abstract No. 100.

A. SH. Revishvili, "A New Coronary Sinus Lead For Left Atrial Pacing and Low–Energy Atrial Defribillation—A Case–Report", 1998, pp. 127–131.

*Primary Examiner*—William E. Kamm
(74) *Attorney, Agent, or Firm*—Venable; Robert Kinberg; Jeffrey W. Gluck

(57) ABSTRACT

Tripolar stimulation of the heart utilizes electrodes implanted in at least two locations in the heart. In a first case, for bi-atrial or bi-ventricular stimulation, electrodes are placed in an appropriate heart chamber and in a blood vessel of the heart. In a second case, electrodes are placed in two separate locations in the same chamber of the heart. In either case, one location is for performing unipolar stimulation (i.e., has electrodes of only a singular polarity), while the other location is for bipolar stimulation (i.e., has electrodes of both positive and negative polarities).

17 Claims, 8 Drawing Sheets

TRIPOLAR STIMULATION OF HEART CHAMBERS

FIELD OF THE INVENTION

The present invention deals with devices for heart stimulation, specifically, implantable defibrillator/pacemakers. In particular, the invention deals with electrode configurations for tripolar stimulation, designed to improve the stimulation characteristics.

BACKGROUND OF THE INVENTION

Large amounts of research have been performed in the area of devices for providing appropriate cardiac stimulation. Such research has resulted in sophisticated technologies for efficient and reliable delivery of stimulation pulses, namely, implantable defibrillator/pacemakers. There are many such devices known in the prior art.

Among the more recent devices are those designed for bi-atrial pacing, in which sensing and stimulation of both the right and left atria is performed. Such an arrangement is particularly useful in patients having unhealthy atrial delays.

References in the literature that deal with earlier questions relating to bi-atrial stimulation and its precursors include:

1. Prakash, A., et al., "Prediction of outcome of chronic single and dual site right atrial pacing for atrial fibrillation prevention by acute electrophysiologic testing," PACE, Vol. 20, Part II, April 1997, Abstract No. 97.
2. Belham, M., et al., "Bi-atrial pacing for atrial fibrillation: where is the optimal site for left atrial pacing," PACE, Vol. 20, Part II, April 1997, Abstract No. 98.
3. Delfaut, P., et al., "Continuous overdrive pacing prevents recurrent atrial fibrillation during single and dual site right atrial pacing," PACE, Vol. 20, Part II, April 1997, Abstract No. 99.
4. Prakash, A., et al., "Multicenter experience with single and dual site right atrial pacing in refractory atrial fibrillation," PACE, Vol. 20, Part II, April 1997, Abstract No. 100.

These references, among many others in the literature, demonstrate the advantages of pacing the atrium from both the right atrium, usually from the atrial appendage, and the left atrium, from the coronary ostium, in preventing the onset of atrial fibrillation.

In addition to bi-atrial stimulation, bi-ventricular stimulation has also been used, particularly in assisting the left ventricle in patients having congestive heart failure.

Prior-art bi-atrial and bi-ventricular pacing have been performed using either:

1. two unipolar (cathodal) electrodes, in the atrium or ventricle (typically, a tip electrode buried in the myocardium) and in the coronary sinus (CS) (floating in the coronary sinus ostium for bi-atrial or in the great cardiac vein for bi-ventricular), with the pacemaker housing used as the reference;
2. two unipolar electrodes (cross-chamber bipolar stimulation), with an atrial/ventricular tip electrode acting as a cathode and a CS ring electrode acting as an anode, or the reverse; or
3. two bipolar sets of electrodes in the atrium/ventricle and in the CS/great cardiac vein.

OBJECTS AND SUMMARY OF THE INVENTION

It is an object of the invention to provide a defibrillator/pacemaker device providing performance superior to prior-art devices.

It is a further object of the invention to implement such a device in a simple, cost-effective manner.

These and other objects of the invention are achieved by the use of tripolar stimulation with a particular electrode configuration. Tripolar stimulation provides the following advantages, respectively, over the above-mentioned prior-art alternatives:

1. Tripolar stimulation exhibits significantly lower impedance at the cost of only a slightly higher pacing threshold;
2. Tripolar stimulation exhibits a much lower pacing threshold, but with greater impedance; however, it should be noted that the threshold in cross-chamber bipolar stimulation is typically so high that the device has no margin left; and
3. Tripolar stimulation has a slightly higher impedance while maintaining the same pacing threshold.

(Note that, in general, higher impedance and lower pacing threshold are desirable, for improved efficiency in pulse delivery/power consumption.)

In particular, the invention is directed toward implanting a heart stimulation device (i.e., pacemaker/defibrillator) for tripolar stimulation. Along with the device, electrodes are implanted in the heart such that electrodes in a heart chamber (i.e., atrium or ventricle) and in a blood conduit to the heart (e.g., the CS or great cardiac vein) have one polarity (i.e., positive [anode] or negative [cathode]) for delivering stimulation pulses, while one or more additional electrodes in the heart chamber have the opposite polarity.

The invention may be used for either bi-atrial or bi-ventricular stimulation, and it can also be extended to dual-site atrial/ventricular stimulation.

In a first embodiment of the invention, a method of implementing tripolar cardiac stimulation in a heart comprises steps of:

(a) implanting a cardiac stimulation device having anodic and cathodic connections and including means for providing electrical stimulation pulses through said anodic and cathodic connections;
(b) electrically connecting first and second electrode lines to respective ones of the anodic and cathodic connections;
(c) electrically coupling at least two electrodes to one of the electrode lines;
(d) electrically coupling at least one electrode to the other electrode line; and
(e) implanting at least one of the at least two electrodes electrically coupled to the one electrode line and the at least one electrode electrically coupled to the other electrode line in a heart chamber; and
(f) implanting at least one other of the at least two electrodes electrically coupled to the one electrode line in a blood vessel of the heart.

In a second embodiment of the invention, a method of implementing tripolar cardiac stimulation in a heart comprises steps of:

(a) implanting a cardiac stimulation device having anodic and cathodic connections and including means for providing electrical stimulation pulses through said anodic and cathodic connections;
(b) electrically connecting first and second electrode lines to respective ones of said anodic and cathodic connections;
(c) electrically coupling at least two electrodes to one of said electrode lines; and (d) electrically coupling at least one electrode to the other one of said electrode lines; and (e) implanting said electrodes in a single heart chamber.

BRIEF DESCRIPTION OF THE DRAWINGS

The invention may be better understood by reference to the subsequent description of the preferred embodiments, in connection with drawings, in which.

DETAILED DESCRIPTION OF THE INVENTION

Figure 1:
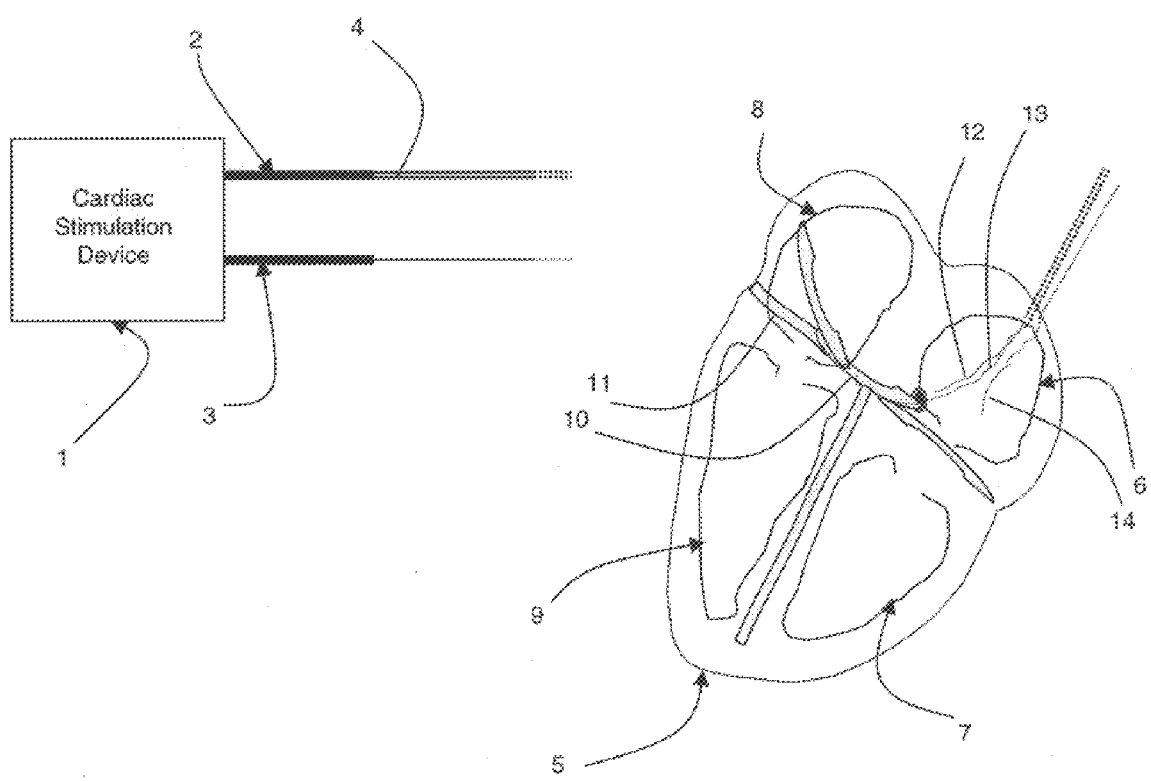
FIG. 1 shows a cardiac stimulation device with electrode leads and their placement in the heart according to an embodiment of the invention.

The present invention is directed to the use of a cardiac stimulation device to provide tripolar heart stimulation. In general, such a device is implanted near the heart, and leads are fed to electrodes that are implanted in the heart. FIG. 1 illustrates such a configuration, according to an embodiment of the invention.

In FIG. 1, cardiac stimulation device 1, which may be a defibrillator, pacemaker or a combination of the two, has lines 2 and 3 that are implanted in a heart 5. Of lines 2 and 3, one is an anodic line, and the other is a cathodic line; for example, line 2 may act as an cathode and line 3 as an anode. In an embodiment of the invention, line 2 is split into two sub-lines 4, which are shown in heart 5 as 12 and 13. Alternatively, lead 3 may be split into two lines (not shown), although the preferred embodiment is to split the cathodic line.

Figure 2:
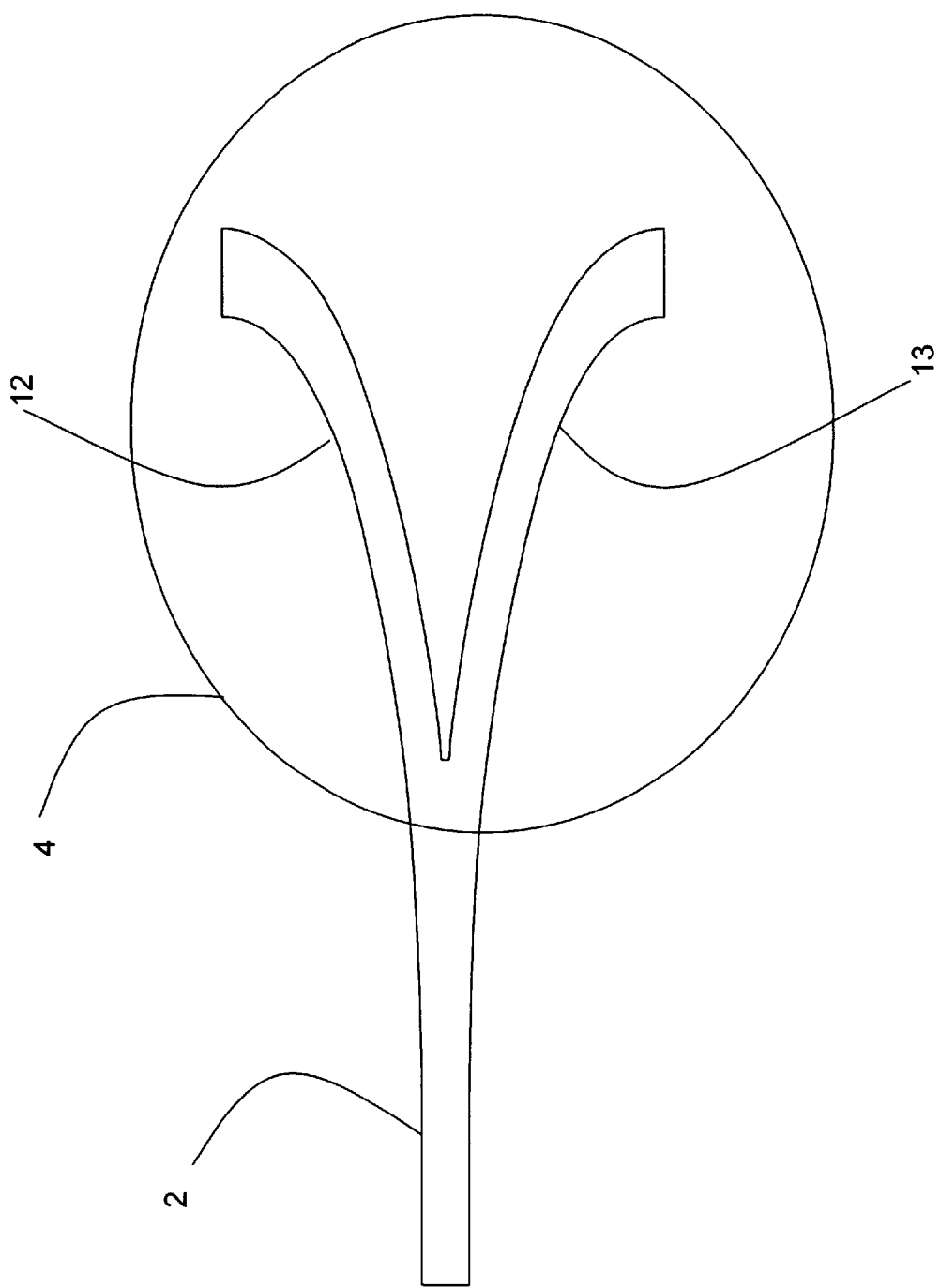
FIG. 2 shows a Y-connector used to "split" an electrode lead according to an embodiment of the invention.

A more detailed depiction of line 2 may be found in FIG. 2. As shown, line 2 is split into leads 12 and 13. Such a splitting may be accomplished, for example, by a Y-connector. By so doing, a single, for example, cathode line is split into two cathode lines. An advantage to using such a Y-connector is that the splitting may be accomplished very simply, using the Y-connector, by a surgeon at the time of implantation. Additionally, such an embodiment does not require any special modification of cardiac stimulation device 1.

Returning to FIG. 1, heart 5, shown in a dorsal view, consists of four chambers, the right and left atria, 6 and 8, respectively, and the right and left ventricles, 7 and 9, respectively.

The present invention may be used for stimulation of any of the heart chambers; in the example shown in FIG. 1, it is being used for bi-atrial pacing. In this example, lead 12, which is a sub-line from line 2, and lead 14, which is an extension of line 3, are implanted in the right atrium 6. Lead 13, the other extension of line 2, is implanted in the coronary sinus (CS) 10. In the preferred embodiment, electrodes located on or forming parts of leads 12 and 13 will act as cathodes, while at least one electrode located on or forming part of lead 14 will act as an anode.

Figure 3:
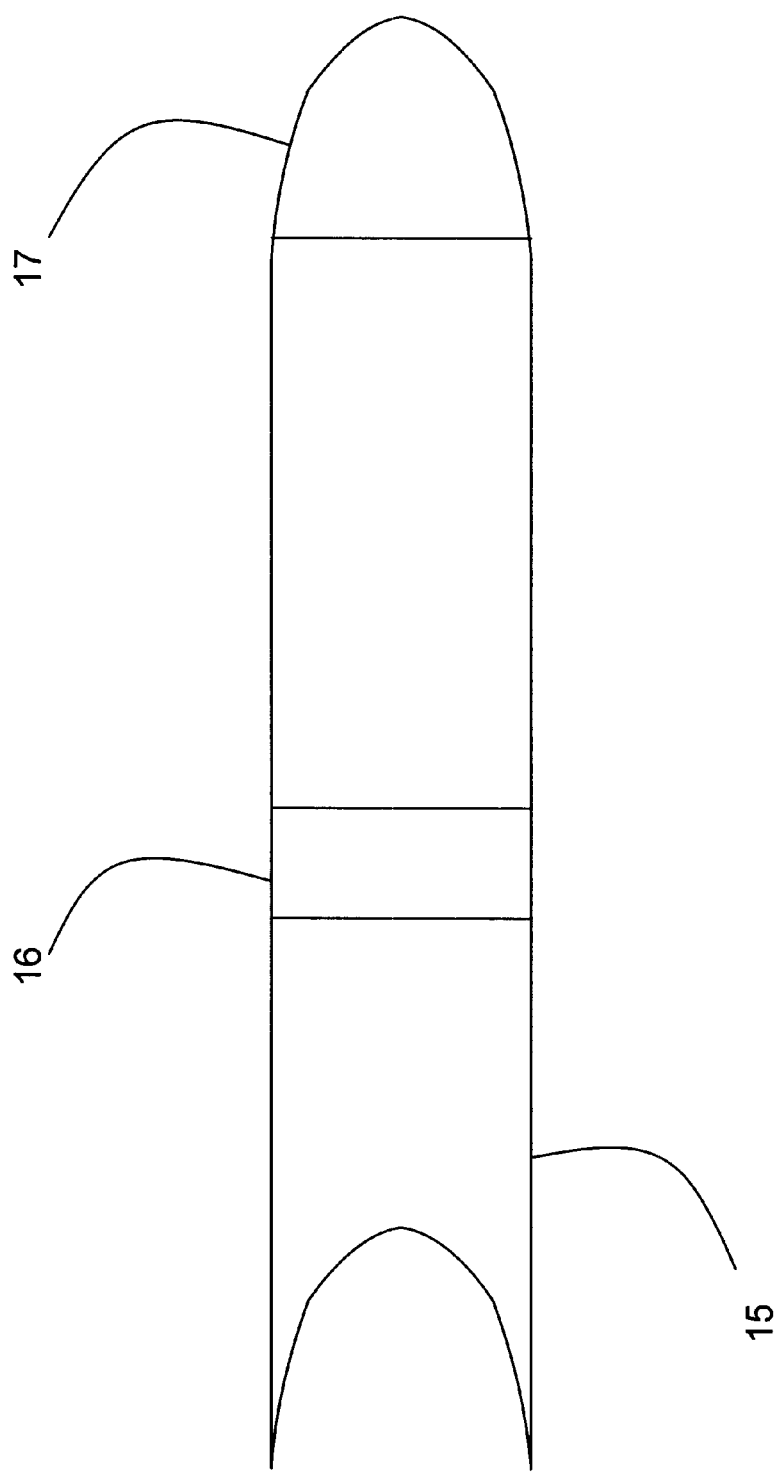
FIG. 3 shows a typical electrode configuration that may be used in an embodiment of the invention.

Leads 12–14 will typically have tip and/or ring electrodes. A tip electrode forms the tip of a lead, while a ring electrode is located along the body of a lead, completely surrounding it. An example of such a lead is shown in FIG. 3. In FIG. 3, lead 15 has a ring electrode 16 and a tip electrode 17. Note that leads 12–14 may have from zero to several ring electrodes and zero or one tip electrode; however, they always have at least one electrode.

In a preferred embodiment of the invention, a tip electrode of a heart chamber lead and one or more electrodes of a heart blood vessel lead are electrically connected and act as a cathode, while a ring electrode of a heart chamber lead acts as an anode.

Implantation of electrodes in the heart chamber (in FIG. 1, the right atrium 6) is performed in a conventional manner. That is to say, the leads of the heart chamber are typically buried into the myocardium and held in place by either a passive fixation arrangement (e.g., fixation tines) or an active fixation arrangement (e.g., a screw).

In contrast, implantation of the lead in a heart blood vessel (in FIG. 1, the CS), is performed differently. Neither active nor passive fixation arrangements are used; if the lead being used has fixation tines, these are clipped prior to implantation. The reason for doing so is to avoid thrombus (i.e., blood clotting), which could endanger the life of the patient. The lead is flexible, and thus, its tip will end up parallel to the wall of the blood vessel. This is shown in FIGS. 4 and 5, for the embodiment of FIG. 1.

Figure 4:
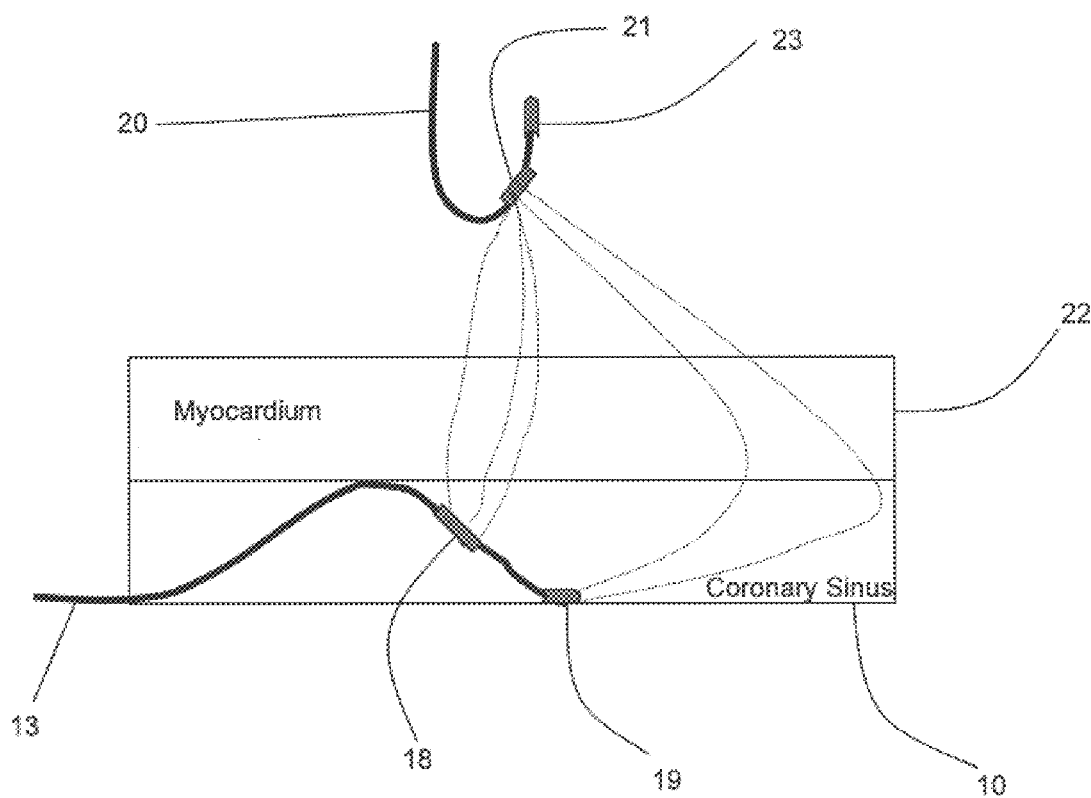
FIG. 4 shows an example of placement of a lead in the CS and conceptually shows flow of current between it and an atrial lead, in an embodiment of the invention.
Figure 5:
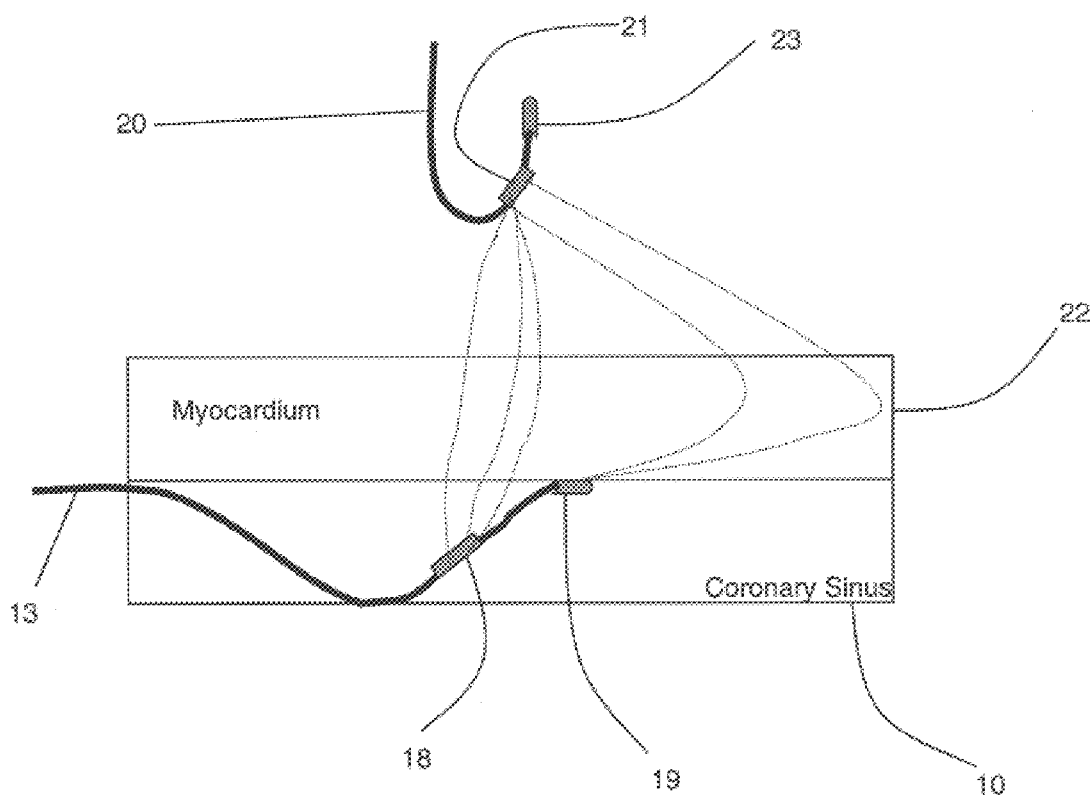
FIG. 5 shows an alternative version of what is shown in FIG. 4.

FIGS. 4 and 5 show the implantation of the lead 13 in the CS 10 and the conduction of electrical current between this lead and an atrial lead (or, more generally, a heart chamber lead) of the opposite polarity. Lead 13 is depicted having a ring electrode 18 and a tip electrode 19; as previously discussed, it may have fewer or additional electrodes. Atrial lead 20 is shown with ring electrode 21 having a polarity opposite that of electrodes 18 and 19 of CS lead 13. Dotted lines conceptually show the path of current flow between electrodes 18 and 19 and electrode 21, through myocardium 22, when an electrical stimulation pulse is applied.

As mentioned above, lead 13 implanted in CS 10 is implanted without a fixation arrangement in the preferred embodiment, and while the tip electrode 19 will end up parallel to the wall of CS 10, there are many ways in which this may happen, noting, for example, the difference in configuration between FIGS. 4 and 5. As shown in FIGS. 4 and 5, the configuration of lead 13, that is, the positions of electrodes 18 and 19, will have some effect on the paths of current conduction between electrodes. However, this has minimal, if any, effect on performance.

Figure 6:
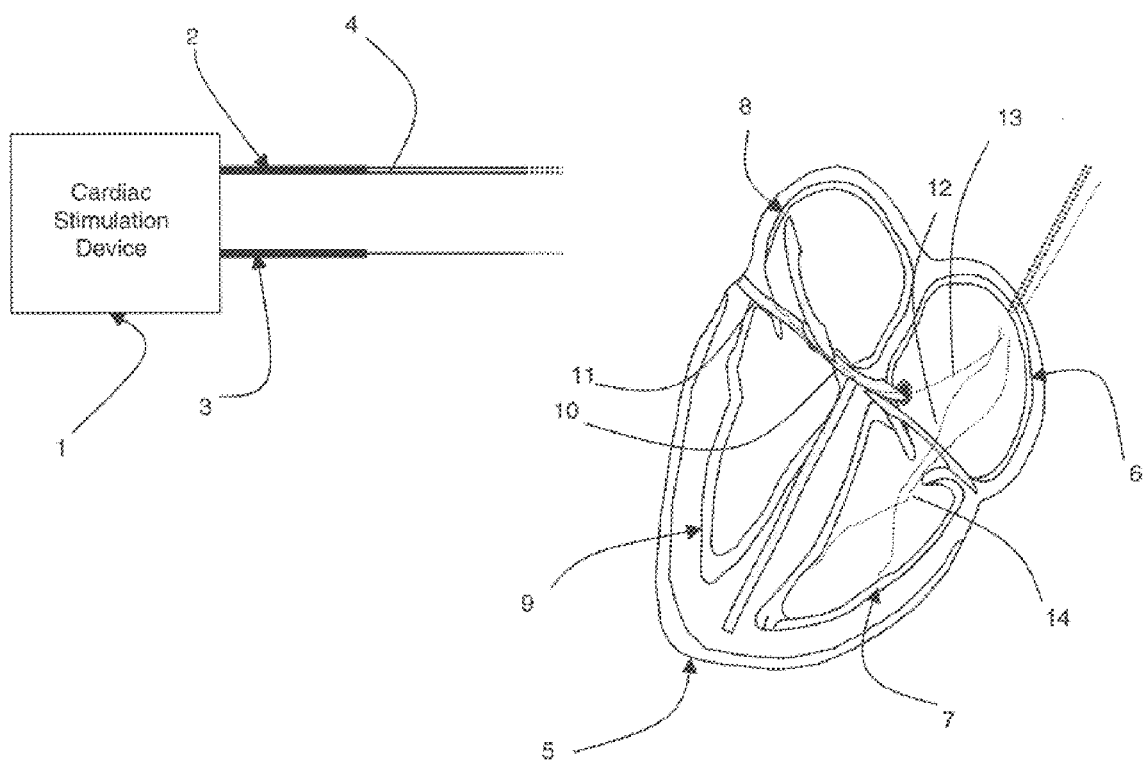
FIG. 6 shows a cardiac stimulation device with electrode leads and their placement in the heart according to another embodiment of the invention.

It is also a preferred embodiment to implant electrode leads to as to effect bi-ventricular tri-polar stimulation. Such a configuration is shown in FIG. 6, in which all of the elements corresponding to elements of FIG. 1 have the same reference labels. In particular, instead of leads 12 and 14 being implanted in an atrium, they are shown implanted in a ventricle (in this case, the right ventricle). In this case, in order to achieve the desired bi-ventricular stimulation, lead 13 is embedded in the great cardiac vein 11, rather than in the CS 10.

In another preferred embodiment of the invention, a single heart chamber lead may be used, instead of two separate heart chamber leads. In this case, the blood vessel lead 13 remains unipolar (i.e., having only a single polarity for all of its electrodes), but the atrial or ventricular lead 12 will be a bipolar lead (i.e., having both anodic and cathodic electrodes); lead 14 does not exist in this embodiment. This embodiment may be implemented using a special Y-connector depicted in FIG. 7. Lines 2 and 3 are fed into Y-connector 24. Inside Y-connector 24, line 2 is split into two branches, 2a and 2b. Branch 2a and line 3 are fed to atrial or ventricular lead 12, while branch 2b is fed to blood vessel lead 13.

Figure 7:
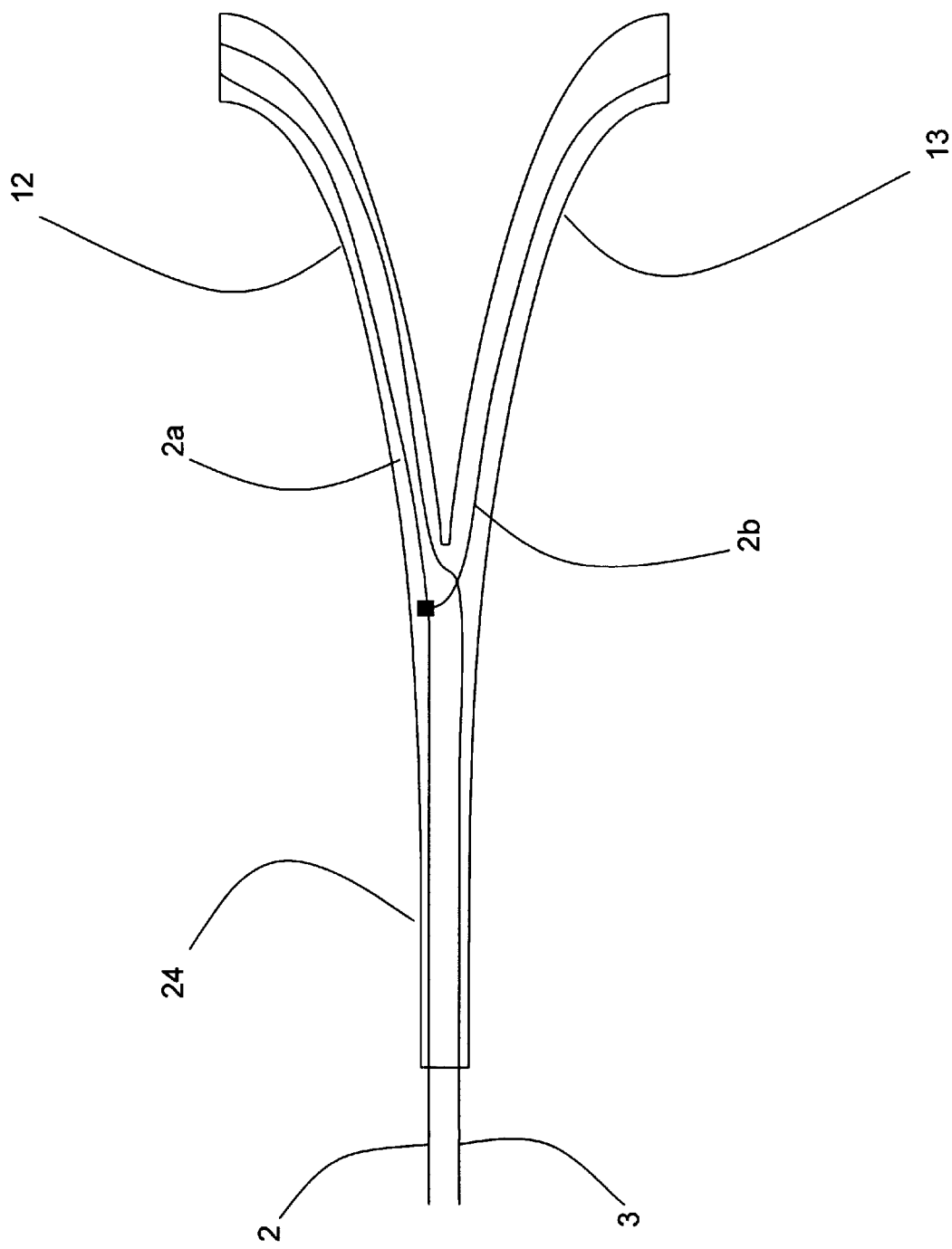
FIG. 7 depicts a Y-connector used in another preferred embodiment of the invention.

Referring to either of FIGS. 4 and 5, in conjunction with FIG. 7, in a preferred embodiment of the invention, line 2 will be a cathode line, and line 3 will be an anode line. In this preferred embodiment, branch 2a is connected to tip electrode 23, while line 3 is connected to ring electrode 21, of an atrial or ventricular lead 12 (shown as 20 in FIGS. 4 and 5). Branch 2b is connected to one or more electrodes of blood vessel lead 13. Thus, ring electrode 21 acts as an anode, while tip electrode 23 and one or more electrodes of blood vessel lead 13 act as cathodic elements.

In another embodiment of the invention, the above concepts of tripolar stimulation may be further applied to performing dual-site pacing in either/both atrium and ventricle. Dual-site pacing is useful in the prevention and treatment of tachyarrythmia. In this embodiment, a bipolar lead and a unipolar lead, as discussed in the immediately preceding two paragraphs, will both be placed in the same atrium or ventricle (in a preferred embodiment, the right atrium or right ventricle), at different locations.

Figure 8:
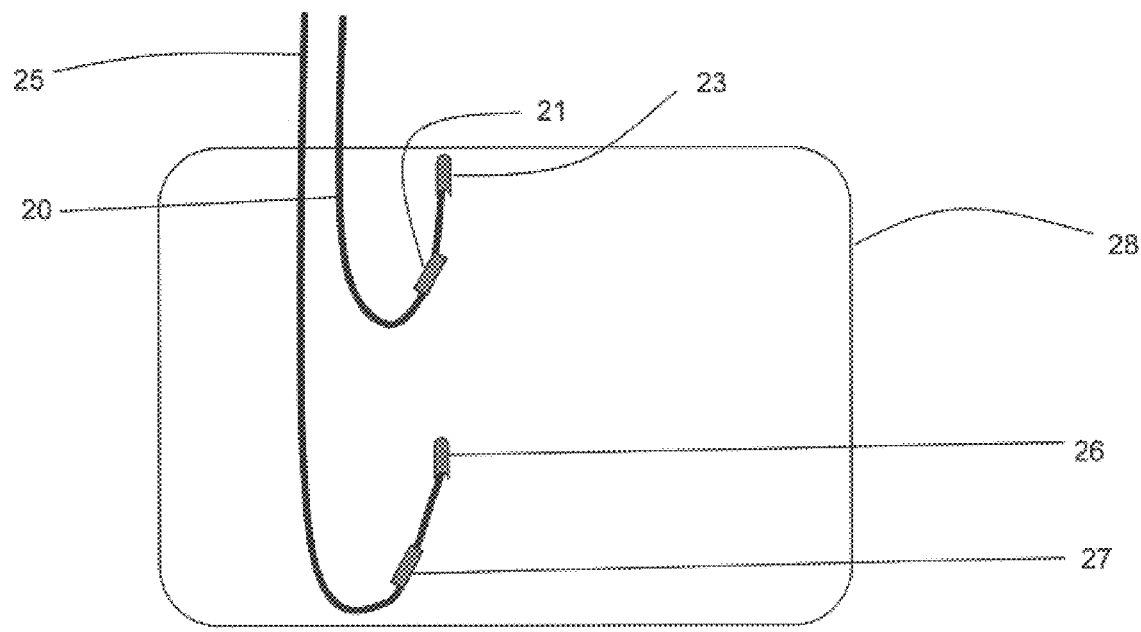
FIG. 8 shows the placement of electrodes for dual-site pacing in another preferred embodiment of the invention.

An implementation of this embodiment is depicted in FIG. 8. FIG. 8 assumes the use of Y-connector 24 of FIG. 7; however, a configuration using a third lead could alternatively be used.

FIG. 8 shows two leads 20 and 25; lead 20 is the same as in FIGS. 4 and 5, as are the tip electrode 23 and the ring electrode 21 shown thereon (recall that lead 20 corresponds to lead 12 of Y-connector 24 in FIG. 7). Lead 25 is shown with tip electrode 26 and ring electrode 27; lead 25 is connected to, or may be considered as corresponding to, lead 13 in FIG. 7. Both leads 20 and 25 are implanted in the same heart chamber 28, preferably using active fixation. In this embodiment, as in the previously discussed embodiment, branch 2a of FIG. 7 is connected to tip electrode 23 of lead 20, while line 3 of FIG. 7 is connected to ring electrode 21 of lead 20. Branch 2b is connected to one or both of electrodes 26 and 27 of lead 25. Note that either or both of leads 20 and 25 may comprise further electrodes, which may or may not be connected to branch 2a, branch 2b or line 3.

In one preferred embodiment, line 2 is cathodic (and hence, so are branches 2a and 2b) and line 3 is anodic, so ring electrode 21 acts as an anode, while the other electrodes shown act as cathodes.

It is to be understood that the above-described embodiments of the invention are merely illustrative of the principles thereof and that numerous modifications and embodiments of the invention may be derived within the spirit and scope thereof, as defined by the claims below.

What is claimed is:

1. A method of implementing tripolar cardiac stimulation in a heart, comprising the steps of:
   (a) implanting a cardiac stimulation device having anodic and cathodic connections and including means for providing electrical stimulation pulses through said anodic and cathodic connections;
   (b) electrically connecting first and second electrode lines to respective ones of the anodic and cathodic connections;
   (c) electrically coupling at least two electrodes to one of the electrode lines;
   (d) electrically coupling at least one electrode to the other electrode line; and
   (e) implanting at least one of the at least two electrodes electrically coupled to the one electrode line and the at least one electrode electrically coupled to the other electrode line in a heart chamber; and
   (f) implanting at least one other of the at least two electrodes electrically coupled to the one electrode line in a blood vessel of the heart.

2. A method as in claim 1, wherein the heart chamber of step (e) is the atrium and the blood vessel of step (f) is the coronary sinus.

3. A method as in claim 2, wherein exactly two electrodes are implanted in the atrium and exactly one electrode is implanted in the coronary sinus.

4. A method as in claim 2, wherein one of the electrodes implanted in the atrium is a ring electrode and the other electrode implanted in the atrium is a tip electrode, and further comprising the step of:
   (g) electrically coupling the ring electrode to the electrode line coupled to the anodic connection.

5. A method as in claim 1, wherein the heart chamber of step (e) is the ventricle and the blood vessel of step (f) is the great cardiac vein.

6. A method as in claim 5, wherein exactly two electrodes are implanted in the ventricle and exactly one electrode is implanted in the great cardiac vein.

7. A method as in claim 5, wherein one of the electrodes implanted in the ventricle is a ring electrode and the second electrode implanted in the ventricle is a tip electrode, and further comprising the step of:
   (g) electrically coupling the ring electrode to the electrode line connected to the anodic connection.

8. A method as in claim 1, wherein step (f) comprises the step of:
   (f1) implanting said at least one other of said at least two electrodes electrically coupled to the one electrode line in said blood vessel of the heart using neither active nor passive fixation.

9. A method as in claim 1, wherein said first electrode line is connected to said anodic connection and said second electrode line is connected to said cathodic connection.

10. A method as in claim 9, further comprising the step of:
   (g) connecting said first and second electrode lines to a Y-connector, said Y-connector splitting said second electrode line into two cathodic sub-lines, one of which is fed through a first output lead of the Y-connector, the other of which is fed through a second output lead of the Y-connector, while said first electrode line is fed through said first output lead of the Y-connector.

11. A method as in claim 10, wherein step (c) comprises the steps of:
   (c1) connecting at least one of said at least electrodes to said cathodic sub-line of said first output lead of the Y-connector; and
   (c2) connecting at least one other of said at least two electrodes to said cathodic sub-line of said second output lead of the Y-connector; and
   wherein step (d) comprises the step of:
   (d1) connecting said at least one electrode to said first electrode line passed through said first output lead of said Y-connector.

12. A method as in claim 11, wherein the heart chamber of step (e) is the atrium and the blood vessel of step (f) is the coronary sinus.

13. A method as in claim 11, wherein the heart chamber of step (e) is the ventricle and the blood vessel of step (f) is the great cardiac vein.

14. A method as in claim 1, further comprising the step of:
(g) connecting one of said first and second electrode lines to a Y-connector, said Y-connector splitting said electrode line into two sub-lines, both of which are separate from the other electrode line.

15. A method as in claim 14, wherein step (c) comprises the steps of:
(c1) connecting at least one of said at least two electrodes to one of said sub-lines; and
(c2) connecting at least one other of said at least two electrodes to the other one of said sub-lines; and wherein step (d) comprises the step of:
(d1) connecting said at least one electrode to the electrode line that was not connected to the Y-connector.

16. A method as in claim 15, wherein the heart chamber of step (e) is the atrium and the blood vessel of step (f) is the coronary sinus.

17. A method as in claim 15, wherein the heart chamber of step (e) is the ventricle and the blood vessel of step (f) is the great cardiac vein.

* * * * *

UNITED STATES PATENT AND TRADEMARK OFFICE
CERTIFICATE OF CORRECTION

PATENT NO. : 6,341,234 B1
DATED : January 22, 2002
INVENTOR(S) : Tran Thong and Max Schaldach It is certified that error appears in the above-identified patent and that said Letters Patent is hereby corrected as shown below:

<u>Title page,</u>
Item [75], the inventor information should read as follows:
-- [75] Inventors: Tran Thong, Portland (OR)
                  Max Schaldach, Erlangen (DE)
                  Amiran Shotaevish Revishvili, Moscow (RU) --

Signed and Sealed this

Eighteenth Day of June, 2002

*Attest:*

*Attesting Officer*

JAMES E. ROGAN
*Director of the United States Patent and Trademark Office*